United States Patent
McKerrecher et al.

(10) Patent No.: US 7,709,505 B2
(45) Date of Patent: May 4, 2010

(54) BENZOFURAN DERIVATIVES, PROCESS FOR THEIR PREPARATION AND INTERMEDIATES THEREOF

(75) Inventors: Darren McKerrecher, Macclesfield (GB); John Wall Rayner, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/534,650

(22) PCT Filed: Nov. 13, 2003

(86) PCT No.: PCT/GB03/04919

§ 371 (c)(1), (2), (4) Date: May 12, 2005

(87) PCT Pub. No.: WO2004/046139

PCT Pub. Date: Jun. 3, 2004

(65) Prior Publication Data

US 2006/0058353 A1  Mar. 16, 2006

(30) Foreign Application Priority Data

Nov. 19, 2002  (GB)  ................. 0226930.6

(51) Int. Cl.
  *A61K 31/443* (2006.01)
  *C07D 405/12* (2006.01)
(52) U.S. Cl. ................. 514/337; 546/284.1
(58) Field of Classification Search ............. 546/284.1; 514/337
See application file for complete search history.

(56) References Cited

U.S. PATENT DOCUMENTS

| | | | |
|---|---|---|---|
| 2,750,393 A | 6/1956 | Elpern |
| 2,967,194 A | 1/1961 | Hauptschein |
| 3,917,625 A | 11/1975 | Lee et al. |
| 3,950,351 A | 4/1976 | Rossignol et al. |
| 4,009,174 A | 2/1977 | Cluzan et al. |
| 4,105,785 A | 8/1978 | Mauvernay et al. |
| 4,146,631 A | 3/1979 | Ford et al. |
| 4,434,170 A | 2/1984 | Dostert et al. |
| 4,474,792 A | 10/1984 | Erickson |
| 4,634,783 A | 1/1987 | Fujii et al. |
| 4,966,891 A | 10/1990 | Fujiu et al. |
| 5,258,407 A | 11/1993 | Washburn et al. |
| 5,273,986 A | 12/1993 | Holland et al. |
| 5,399,702 A | 3/1995 | Holland et al. |
| 5,466,715 A | 11/1995 | Washburn et al. |
| 5,510,478 A | 4/1996 | Sabb |
| 5,661,153 A | 8/1997 | Isobe et al. |
| 5,672,750 A | 9/1997 | Perry |
| 5,712,270 A | 1/1998 | Sabb |
| 5,849,735 A | 12/1998 | Albright et al. |
| 6,110,945 A | 8/2000 | Head et al. |
| 6,197,798 B1 | 3/2001 | Fink et al. |
| 6,200,995 B1 | 3/2001 | De la Brouse-Elwood et al. |
| 6,207,693 B1 | 3/2001 | Setoi et al. |
| 6,214,878 B1 | 4/2001 | Bernardon et al. |
| 6,242,474 B1 | 6/2001 | Yamasaki et al. |
| 6,255,335 B1 | 7/2001 | Himmler et al. |
| 6,316,482 B1 | 11/2001 | Setoi et al. |
| 6,320,050 B1 | 11/2001 | Bizzarro et al. |
| 6,348,474 B1 | 2/2002 | Kayakiri et al. |
| 6,369,229 B1 | 4/2002 | Head et al. |
| 6,376,515 B2 | 4/2002 | Zhu et al. |
| 6,388,071 B2 | 5/2002 | Mahaney |
| 6,448,399 B1 | 9/2002 | Corbett et al. |
| 6,486,349 B1 | 11/2002 | Flitter et al. |
| 6,528,543 B1 | 3/2003 | Bizzarro et al. |
| 6,545,155 B2 | 4/2003 | Corbett et al. |
| 6,610,846 B1 | 8/2003 | Bizzarro et al. |
| 6,613,942 B1 | 9/2003 | Ling et al. |
| 7,132,546 B2 | 11/2006 | Kato et al. |
| 7,199,140 B2 | 4/2007 | Hayter et al. |
| 7,230,108 B2 | 6/2007 | Hargreaves et al. |
| 2001/0027200 A1 | 10/2001 | De la Brouse-Elwood et al. |
| 2002/0002183 A1 | 1/2002 | Zhu et al. |
| 2002/0095044 A1 | 7/2002 | Jagtap et al. |
| 2003/0162690 A1 | 8/2003 | Zhu et al. |
| 2004/0014968 A1 | 1/2004 | Bizzarro et al. |
| 2004/0077555 A1 | 4/2004 | Ishihara et al. |
| 2005/0080106 A1 | 4/2005 | Boyd et al. |

(Continued)

FOREIGN PATENT DOCUMENTS

CA  2605738  11/2006

(Continued)

OTHER PUBLICATIONS

Balant et al., "Metabolic Considerations, etc.," Burger's Medicinal Chemistry, 5ed, 1, Wollf ed. NY: John Wiley & Sons, 1995, pp. 949-982.*

(Continued)

*Primary Examiner*—Patricia L Morris
(74) *Attorney, Agent, or Firm*—Morgan, Lewis & Bockius LLP

(57) ABSTRACT

Compound of formula (I) wherein A is selected from pyridin-2-yl or thiazol-2-yl and $R^1$, $R^2$ and $R^3$ are as described in the specification and their use in the treatment or prevention of a disease or medical conditions mediated through glucokinase.

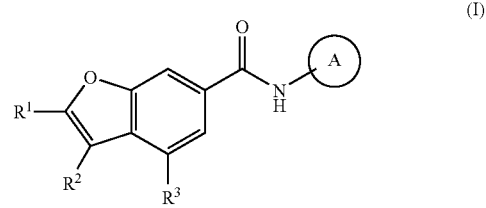

(I)

8 Claims, No Drawings

U.S. PATENT DOCUMENTS

| | | |
|---|---|---|
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0167053 A1 | 7/2006 | Iino et al. |
| 2006/0258728 A1 | 11/2006 | Tani et al. |
| 2007/0078168 A1 | 4/2007 | Caulkett |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1336607 A1 | 8/2003 |
| EP | 1357116 | 10/2003 |
| EP | 1400540 | 3/2004 |
| EP | 1 496 052 A1 | 1/2005 |
| EP | 1600442 | 11/2005 |
| EP | 1702919 | 9/2006 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| GB | 2385328 A | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO-00/58293 A1 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO-01/20327 A1 | 3/2001 |
| WO | WO 01/26652 | 4/2001 |
| WO | WO 01/32639 | 5/2001 |
| WO | WO-01/44216 | 6/2001 |
| WO | WO-01/44216 A1 | 6/2001 |
| WO | WO 01/64642 | 9/2001 |
| WO | WO 01/64643 | 9/2001 |
| WO | WO 01/74791 | 10/2001 |
| WO | WO-01/83465 A2 | 11/2001 |
| WO | WO-01/83478 A2 | 11/2001 |
| WO | WO-01/85706 A1 | 11/2001 |
| WO | WO-01/85707 A1 | 11/2001 |
| WO | WO 02/00633 | 1/2002 |
| WO | WO-02/08209 A1 | 1/2002 |
| WO | WO-02/14312 A1 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO-02/46173 A1 | 6/2002 |
| WO | WO-02/48106 A2 | 6/2002 |
| WO | WO 02/051831 | 7/2002 |
| WO | WO 02/064545 | 8/2002 |
| WO | WO 02/079145 | 10/2002 |
| WO | WO-03/000262 A1 | 1/2003 |
| WO | WO-03/000267 A1 | 1/2003 |
| WO | WO 03/015518 | 2/2003 |
| WO | WO-03/015774 A1 | 2/2003 |
| WO | WO-03/022856 A1 | 3/2003 |
| WO | WO 03/024222 | 3/2003 |
| WO | WO 03/026652 | 4/2003 |
| WO | WO 03/028641 | 4/2003 |
| WO | WO-03/047626 A1 | 6/2003 |
| WO | WO 03/048152 | 6/2003 |
| WO | WO 03/051366 | 6/2003 |
| WO | WO-03/055482 A1 | 7/2003 |
| WO | WO 03/066613 | 8/2003 |
| WO | WO-03/080585 A1 | 10/2003 |
| WO | WO 03/082838 | 10/2003 |
| WO | WO-03/095438 A1 | 11/2003 |
| WO | WO-03/097824 A1 | 11/2003 |
| WO | WO-2004/002481 A1 | 1/2004 |
| WO | WO 2004/022536 | 3/2004 |
| WO | WO 2004/031179 | 4/2004 |
| WO | WO 2004/045614 | 6/2004 |

| | | |
|---|---|---|
| WO | WO-2004/045614 A1 | 6/2004 |
| WO | WO-2004/046139 A1 | 6/2004 |
| WO | WO-2004/050645 A1 | 6/2004 |
| WO | WO-2004/052869 A1 | 6/2004 |
| WO | WO-2004/063179 A1 | 7/2004 |
| WO | WO-2004/063194 A1 | 7/2004 |
| WO | WO-2004/072031 A2 | 8/2004 |
| WO | WO-2004/072066 A1 | 8/2004 |
| WO | WO-2004/076420 A1 | 9/2004 |
| WO | WO-2004/081001 A1 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO-2005/044801 A1 | 5/2005 |
| WO | WO 2005/048953 | 6/2005 |
| WO | WO-2005/049019 A1 | 6/2005 |
| WO | WO-2005/054200 A1 | 6/2005 |
| WO | WO-2005/054233 A1 | 6/2005 |
| WO | WO-2005/056530 A1 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/031739 | 3/2007 |
| WO | WO 2007/053657 | 5/2007 |
| WO | WO 2007/060448 | 5/2007 |
| WO | WO 2008/050101 | 5/2007 |
| WO | WO 2008/050117 | 5/2008 |
| WO | WO 2008/075073 | 6/2008 |

OTHER PUBLICATIONS

McKerrecher et al., "Identification of Orally Bioavailable Small Molecule Activators of Glucokinase," 12th SCI-RSC Medicinal Chemistry Symposium, Cambridge, UK, Sep. 7-10, 2003.

McKerrecher et al. "Design and synthesis of novel glucokinase activators as potential treatment for type 2 diabetes" Abstract plus slides, Frontiers in Medicinal Chemistry, Frankfurt (Mar. 2006).

McKerrecher et al. "Identification of orally bioavailable small molecule activators of glucokinase" Abstract, Anglo-Swedish Medicinal Chemistry Meeting (Mar. 2005).

Alvarez et al., "Expression of the Glucagon-Like Peptide-1 Receptor Gene in Rat Brain," Journal of Neurochemistry 66(3):920-927 (1996).

Alvarez et al., "Evidence that Glucokinase Regulatory Protein is Expressed and Interacts with Glucokinase in Rat Brain," Journal of Neurochemistry 80:45-53(2002).

Bell et al., "Glucokinae Mutations, Insulin Secretion, and Diabetes Mellitus," Annu. Rev. Physiol. 58:171-186 (1996).

Brocklehurst et al., "Stimulation of Hepatocyte Glucose Metabolism by Novel Small Molecule Glucokinase Activators," Diabetes 53:535-541 (2004).

Caro et al., "Liver Glucokinase: Decreased Activity in Patients with Type II Diabetes," Horm. Metab. Res. 27:19-22 (1995).

Christesen et al., "The Second Activating Glucokinase Mutation (A456V) Implications for Glucose Homeostasis and Diabetes Therapy," Diabetes 51:1240-1246 (2002).

Corbett, "Track 3—Mastering Medicinal Chemistry: Applying Organic Chemistry to Biological Problems, Success Stories in Medicinal Chemistry," Molecular Medicine Tri-Conference, Moscone West Convention Center, San Francisco California, Mar. 26, 2005—11:00-11:30 Glucokinase Activators: Discovery of Novel, Orally Active Glucse Lowering Agents, Mar. 24-26, 2004.

DeFronzo, "The Triumvirate: β-Cell, Muscle, Liver—A Collusion Responsible for NIDDM," Diabetes 37:667-687 (1988).

Desai et al., "Phenotypic correction of Diabetic Mice by Adenovirus-Mediated Glucokinase Expression," Diabetes 50:2287-2295 (2001).

Ferre et al., "Correction of Diabetic Alteractions by Glucokinase," Proc. Natl. Acad. Sci. USA 93:7225-7230 (1996).

Froguel et al., "Familial Hyperglycemia Due to Mutations in Glucokinase—Definition of a Subtype of Diabetes Mellitus," The New England Journal of Medicine 328(10):697-702 (1993).

Fujimoto et al., "Administration of D-Glucosamine into the Third Cerebroventricle Induced Feeding Accompanied by Hyperglycemia in Rats," Life Sciences 37(26):2475-2482 (1985).

Glaser et al., "Familial Hyperinsulinism Caused by an Activating Glucokinase Mutation," The New England Journal of Medicine 338(4):226-230 (1998).

Grimsby et al., "Allosteric Activators of Glucokinase: Potential Role in Diabetes Therapy," Science 301:370-373 (2003).

Grimsby, "Glucokinase Activators—Potential Treatment for Type 2 Diabetes," Roche—SMi Diabetes London UK pp. 28-29 (2002.

Kurata et al., "Structural Evaluation of Glucose Analogues on Feeding Elicitation in Rat," Metabolism 38(1):46-51 (1989).

Kurata et al., "D-Glucose Suppression of Eating After Intra-Third Ventricle Infusion in Rat," Physiology & Behavior 37:615-620 (1986).

Levin, "Glucosensing Neurons do More Than Just Sense Glucose," International Journal of Obesity 25(5):S68-S72 (2001).

Levin et al., "Differential Effects of Diet and Obesity on High and Low Affinity Sulfonylurea Binding Sites in the Rat Brain," Brain Research 739:293-300 (1996).

Levin et al., "In vivo and in vitro Regulation of [$^3$H] Glyburide Binding to Brain Sulfonylurea Receptors in Obesity-Prone and Resistant Rats by Glucose," Brain Research 776:146-153 (1997).

Levin et al., "Brain Glucose Sensing and body Energy Homeostasis: Role in Obesity and Diabetes," A. J. of Physiology 276:R1223-R1231 (1999).

Levin et al., "Reduced Glucose-Induced Neuronal Activation in the Hypothalamus of Diet-Induced Obese Rats," Brain Research 808:317-319 (1998).

Lynch et al., "Localization of Glucokinase Gene Expression in the Rat Brain," Diabetes 49:693-700 (2000).

McKerrecher et al., "Discovery, Synthesis and Biological Evaluation of Novel Glucokinase Activators," Bioorganic & Medicinal chemistry Letters 15:2103-2106 (2005).

Mobbs et al., "Brain Glucose-Sensing Mechanisms: Ubiquitous Silencing by Aglycemia vs. Hypothalamic Neuroendocrine Responses," Am. J. Physiol. Endocrinol. Metab. 281:E649-E654 (2001).

Moore et al., "Acute Fructose Administration Improves Oral Glucose Tolerance in Adults with Type 2 Diabetes," Diabetes Care 24(11):1882-1887 (2001).

Printz et al., "Mammalian Glucokinase," Annu. Rev. Nutr. 13:463-496 (1993).

Qian-Cutrone et al., "Glucolipsin A and B, Two New Glucokinase Activators Producted by Streptomyces purpurogeniscleroticus and Nocardia vaccinii," The Journal of Antibiotics 52(3):245-255 (1999).

Roncero et al., "Functional Glucokinase Isoforms are Expressed in Rat Brain," Journal of Neurochemistry 74(5):1848-1857 (2000).

Rowe et al., "Potassium Channel Dysfunction in Hypothalamic Glucose-Receptive Neurones of Obese Zucker Rats," Journal of Physiology 497(2):365-377 (1996).

Schuit at al., "Perspectives in Diabetes—Glucose Sensing in Pancreatic β-Cells—A Model for the Study of Other Glucose-Regulated Cells in Gut, Pancreas, and Hypothalamus," Diabetes 50:1-11 (2001).

Seoane et al., "Glucokinase Overexpression Restores Glucoes Utilization and Storage in Cultured Hepatocytes from Male Zucker Diabetic Fatty Rats," The Journal of Biological Chemistry 274(45):31833-31838 (1999).

Shiota et al., "Glucokinase Gene Locus Transgenic Mice are Resistant to the Development of Obesity-Induced Type 2 Diabetes," Diabetes 50:622-629 (2001).

Spanswick et al., "Insulin Activates ATP-Sensitive $K^+$ Channels in Hypothalamic Neurons of Lean, but Not Obese Rats," Nature Neuroscience 3(8):757-758 (2000).

Spanswick et al., "Leptin Inhibits Hypothalamic Neurons by Activation of ATP-Senstive Potassium Channels," Nature 390:521-525 (1997).

Velho et al., "Impaired Hepatic Glycogen Synthesis in Glucokinase-Deficient (MODY-2) Subjects," J. Clin. Invest. 98:1755-1761 (1996).

Yang et al., "Hypothalamic Glucose Sensor—Similarities to and Differences from Pancreatic β-Cell Mechanisms," Diabetes 48:1763-1772 (1999).

Carroll et al., Stress, Signalling and Control, Biochemical Society Meeting 679 Jul. 2-4, 2003.

Anderson et al "Pyridopyrimidines. 6. Nucleophilic substitutions in the pyrido[2,3-d]pyrimidine series" J. Org. Chem. 42(6):993-996 (1977).

Ando et al. "Fluoride salts on alumina as reagents for alkylation of phenols and alcohols" Bull. Chem. Soc. Jpn. 55(8):2504-2507 (1982).

Atwell et al. "Potential antitumor agents. VI. Bisquaternary salts" J. Med. Chem. 11(2):295-300 (1968).

Baker et al. "Structure and synthesis of Pallescansin E utilising a modified Wadsworth-Emmons reaction" J. Chem. Soc., Perkin Trans. 1, 12:3087-3091 (1981).

Baker et al. "Synthesis of Pallescensin-E: Use of crown ether in the Wadsworth procedure for olefin formation" Tetrahedron Letters 22:161-162 (1981).

Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).

Beilstein Registry No. 6511458 (Apr. 18, 1994) [XP002272206].

Beller et al. "Photochemical synthesis of benzo[f]quinolines" J Org Chem. 42(22):3514-3518 (1977).

Berl et al. "Induced fit selection of a barbiturate receptor from a dynamic structural and conformational/ configurational library" European J. Org. Chem. (11):3089-3094 (1999).

Berl et al. "Template-induced and molecular recognition directed hierarchical generation of supramolecular assemblies from molecular strands" Chem. Eur. J. 6(11):1938-1946 (2000).

Bonina et al. "Synthesis and pharmacologic activity of 2-arylethenylthiazol-4-acetic and 4-carboxylic acids" II Farmaco 40(11):875-884 (1985).

Boucherle et al. "Recherches dans la serie des cetones polyphenoliques IV. Thiazoles" Chimica. Therapeutica. 3(5):360-363 (1968) (Translation enclosed).

Bowden et al. "Structure-activity relations. Part 10. Metal-ion-complexation studies of a series of substituted benzamidotetrazoles" J. Chem. Research (Synopses) 11:304(1991).

Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).

Brenner et al. "Imino-bridged heterocycles. VII. (1) N-aminobenzocycloheptapyridinimines" J. Heterocyclic Chem. 23:1331-1332 (1986).

Caulfield et al. "The first potent and selective inhibitors of the glycine transporter type 2" J. Med. Chem. 44(17):2679-2682 (2001).

Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).

Chemical Abstracts Service, Columbus, Ohio, US: CAS Registry No. 438028-05-8 (Nov. 15, 2001); CAS Registry No. 438024-90-9 (Nov. 15, 2001), [XP002272448].

Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].

Chemical Abstracts Service, Columbus, Ohio, US: CAS Registry No. 354767-51-4 (Sep. 5, 2001).

Chemical Abstracts Service, Columbus, Ohio, US: CAS Registry No. 354767-66-1 (Sep. 5, 2001).

Ciaceri et al. "Analgesic, antipyretic and anti-inflammatory action of some new acids of the phenylethylenethiazole series" Minerva Medica 63(42):2409-2413 (1972).

Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coghlan et al., "Glucokinase activators in diabetes management" Expert Opin. Investig. Drugs 17(2):145-167 (2008).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeJohn et al. "Functionalization of Substituted 2(1H)- and 4(1H)-Pyridones. III. The preparation of substituted 6-vinyl-1,2-dihydro-2-oxo-- and 1,4-dihydro-4-oxo-3-pyridinecarboxylic acids through the chemistry of pyridone dianions" J. Heterocyclic Chem. 20(5):1295-1302 (1983).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22: 1686 (1957).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Gorman et al. "Effect of high-fat diet on glucose homeostasis and gene expression in Glucokinase (GK) heterozygous knock-outs" Abstract No. 0108-OR, 67th Annual Scientific Sessions, American Diabetes Association, Chicago, IL (Jun. 22-26, 2007).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution" " Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel antidiabetic agents" Biochemical Society Transactions 33(Part 2):371-374 (2005).

Leighton, "Pre-clinical disease models—challenges and success stories" 44th Drug Information Association Annual Meeting, Boston, MA, US (2008).

Levkoev et al. "Research on cyanide dyes 11. 7,7'-Dimethylthiacarbocyanines" Zhurnal Obshchei Khimii 27:3097-3107 (1957) (Translation enclosed).

Lith, "Evaluation of the effects on whole body glucose metabolism after single doses of X2000—A glucose lowering agent" Poster presentation, Master thesis in Pharmaceutical Bioscience, Goteborgs University (2008).

Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polypyrimidine receptors" Angewandte Chemie International Edition 39(3):551-554 (2000).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design of a potent, soluble glucokinase activator with excellent in vivo efficacy" Bioorg. Med. Chem. Lett. 16(10):2705-2709 (May 15, 2006) Epub Feb 28, 2006.

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

Meijer et al "Chiral amplification in supramolecular stacks" Polymer Preprints 41(1):902-903 (2000).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328-7336 (1998).

Palmans "Extended-core discotic liquid crystals based on the intramolecular H-bonding in N-acylated 2,2'-bipyridine-3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Ralph et al. "Glucose Modulation of Glucokinase Activation by Small Molecules" Biochemistry 47(17):5028-5036 (2008).

Rivalle et al. "2,3 Disubstituted furans and pyrroles-XVIII: Synthesis annd rearrangement of 4H-dihydro-9,10 benzo[4,5]cyclohepta[1,2-b]furannones-4" Tetrahedron 32(7):829-834 (1976).

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

Rogers et al. "Mesoionic purinone analogues as inhibitors of cyclic-AMP phosphodiesterase: a comparison of several ring systems" J. Med. Chem. 24(11):1284-1287 (1981).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Shorvon, "Pyrrolidone derivatives" Lancet 358(9296):1885-1892 (2001).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 (1997).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" .J Am. Chem. Soc. 124(49):14759-14769 (2002).

Vanderstelt et al. "Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch. 22(1):133-137 (1972).

Vertigan et al. "Impact of cell glycogen content on modulation of hepatocyte glucose metabolism by pharmacological agents" Diabetologia, 47 Supp 1, A 214, 589 (2004).

West, Anthony R., "Solid State Chemistry and its Applications" Wiley, New York, pp. 358 and 365 (1988).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).

Wolff, Manfred E. "Burger's Medicinal Chemistry", 5th Edition, Part I, John Wiley & Sons, pp. 975-977 (1995).

Yakushijin et al. "Intramolecular ring formation of phenyl azide and furan" Heterocycles 12(8):1021-1026 (1979).

Yakushijin et al. "Intramolecular ring formation of phenyl azide and furan moieties" Chem. Pharm. Bull. 30(1):140-151 (1982).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

* cited by examiner

BENZOFURAN DERIVATIVES, PROCESS FOR THEIR PREPARATION AND INTERMEDIATES THEREOF

RELATED APPLICATIONS

This application is a national stage filing under 35 U.S.C. 371 of International Application PCT/GB2003/004919, filed Nov. 13, 2003, which claims priority from United Kingdom Application No. 0226930.6, filed Nov. 19, 2002, the specifications of each of which are incorporated by reference herein. International Application PCT/GB2003/004919 was published under PCT Article 21(2) in English.

The present invention relates to chemical compounds useful in the treatment or prevention of a disease or medical conditions mediated through glucokinase (GLK), leading to a decreased glucose threshold for insulin secretion. In addition the compounds are predicted to lower blood glucose by increasing hepatic glucose uptake. Such compounds may have utility in the treatment of type 2 diabetes and obesity. The invention also relates to processes for preparing said compounds, pharmaceutical compositions comprising said compounds, and the use of such a compound in the conditions described above.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6-10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, type 2 maturity-onset diabetes of the young (MODY-2), the diabetes is caused by GLK loss of function mutations [3, 4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9-12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is elevated in the post-absorptive state whereas F1P predominates in the post-prandial state. In contrast to the hepatocyte, the pancreatic β-cell expresses GLK in the absence of GLKRP. Therefore, β-cell GLK activity is regulated exclusively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act exclusively in the liver. However, compounds with either profile are predicted to be of therapeutic benefit in treating type 2 diabetes as this disease is characterised by defective glucose utilisation in both tissues.

GLK and GLKRP and the $K_{ATP}$ channel are expressed in neurones of the hypothalamus, a region of the brain that is important in the regulation of energy balance and the control of food intake [14-18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23-28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "diabesity" target (of benefit in both Diabetes and Obesity).

In WO 00/58293 and WO 01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described below. Compounds of the present invention may activate GLK directly or may activate GLK by inhibiting the interaction of GLKRP with GLK. Many compounds of the present invention may show favourable selectivity compared to known GLK activators.

International application number: WO03/000267 describes a group of benzoyl amino pyridyl carboxylic acids which are activators of the enzyme glucokinase (GLK), International application number WO03/015774 describes a group of benzoylamino heterocycle compounds as glucokinase activators and International application number WO03/000262 describes a group or vinyl phenyl derivatives as glucokinase activators.

According to the present invention there is provided a compound of formula (I):

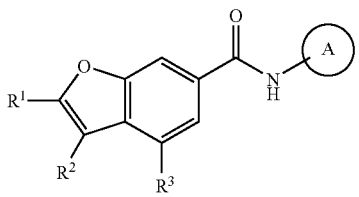

(I)

wherein:

Ring A is pyridin-2-yl or thiazol-2-yl; wherein said pyridin-2-yl or thiazol-2-yl may be optionally substituted on carbon by one or more groups selected from $R^4$;

One of $R^1$ and $R^2$ is hydrogen and the other is hydrogen or $C_{1-4}$alkyl; wherein $R^1$ and $R^2$ may be substituted on carbon by one or more groups selected from $R^5$;

$R^3$ is selected from $C_{1-4}$alkyl, $C_{1-4}$alkoxy, carbocyclyl, heterocyclyl, carbocyclyloxy and heterocyclyloxy; wherein $R^3$ may be independently optionally substituted on carbon by one or more groups selected from $R^6$; and wherein if said heterocyclyl contains an —NH— moiety that nitrogen may be optionally substituted by $C_{1-4}$alkyl;

$R^4$ is selected from halo, carboxy and $C_{1-4}$alkyl;

$R^5$ and $R^6$ are independently selected from halo, $C_{1-4}$alkyl, $C_{1-4}$alkoxy, N—($C_{1-4}$alkyl)amino, N,N—($C_{1-4}$alkyl)$_2$amino, carbocyclyl, heterocyclyl, carbocyclyloxy, heterocyclyloxy and carbocyclylidenyl; wherein $R^5$ and $R^6$ may be independently optionally substituted on carbon by one or more $R^7$; and wherein if said heterocyclyl contains an —NH— moiety that nitrogen may be optionally substituted by $C_{1-4}$alkyl;

$R^7$ is selected from halo, carboxy, methyl, ethyl, methoxy, ethoxy, methylamino, ethylamino, dimethylamino, diethylamino and N-methyl-N-ethylamino;

or a salt, solvate or pro-drug thereof.

Compounds of formula (I) may form salts which are within the ambit of the invention. Pharmaceutically acceptable salts are preferred although other salts may be useful in, for example, isolating or purifying compounds.

The term "halo" includes chloro, bromo, fluoro and iodo; preferably chloro, bromo and fluoro; most preferably fluoro.

In this specification the term "alkyl" includes both straight and branched chain alkyl groups. For example, "$C_{1-4}$alkyl" and "$C_{1-6}$alkyl" includes propyl, isopropyl and t-butyl.

A "carbocyclyl" is a saturated, partially saturated or unsaturated, mono or bicyclic carbon ring that contains 3-12 atoms; wherein a —CH$_2$— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclohexyl or phenyl. Most particularly phenyl.

A "heterocyclyl" is a saturated, partially saturated or unsaturated, monocyclic or bicyclic ring containing 3-12 atoms of which at least one atom is chosen from nitrogen, sulphur or oxygen, wherein a —CH$_2$— group can optionally be replaced by a —C(O)— or sulphur atoms in a heterocyclic ring may be oxidised to S(O) or S(O)$_2$. A heterocyclyl ring may, unless otherwise specified, be carbon or nitrogen linked, unless linking via nitrogen leads to a quaternary nitrogen. Preferably a "heterocyclyl" is a saturated, partially saturated or unsaturated, monocyclic or bicyclic ring wherein each ring contains 5 or 6 atoms of which 1 to 3 atoms are nitrogen, sulphur or oxygen, which may, unless otherwise specified, be carbon or nitrogen linked, wherein a —CH$_2$— group can optionally be replaced by a —C(O)— or sulphur atoms in a heterocyclic ring may be oxidised to S(O) or S(O)$_2$ groups. More preferably a "heterocyclyl" is a saturated, partially saturated or unsaturated, monocyclic ring wherein each ring contains 5 or 6 atoms of which 1 to 3 atoms are nitrogen, sulphur or oxygen. Further preferably a "heterocyclyl" is a partially saturated or unsaturated monocyclic ring wherein each ring contains 5 or 6 atoms, preferably 5 atoms, of which 1 to 2 atoms are nitrogen, sulphur or oxygen.

Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, isoxazolyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiazolyl, thiadiazolyl, isothiazolyl, 1,2,4-triazolyl, 1,2,3-triazolyl, pyranyl, indolyl, pyrimidyl, thiazolyl, pyrazinyl, pyridazinyl, pyridyl, 4-pyridonyl, quinolyl and 1-isoquinolonyl. Preferably the term "heterocyclyl" refers to monocyclic heterocyclic rings with 5- or 6-membered systems, such as isoxazolyl, pyrrolidinyl, 2-pyrrolidonyl, 2,5-dioxopyrrolidinyl, morpholino, tetrahydrofuranyl, piperidyl, piperazinyl, thiomorpholino, tetrahydropyranyl, thienyl, imidazolyl, 1,2,4-triazolyl, 1,3,4-triazolyl, indolyl, thiazolyl, thiadiazolyl, pyrazinyl, pyridazinyl and pyridyl. Preferred examples of 5/6 and 6/6 bicyclic ring systems include benzofuranyl, benzimidazolyl, benzthiophenyl, benzthiazolyl, benzisothiazolyl, benzoxazolyl, benzisoxazolyl, pyridoimidazolyl, pyrimidoimidazolyl, quinolinyl, isoquinolinyl, quinoxalinyl, quinazolinyl, phthalazinyl, cinnolinyl and naphthyridinyl.

Examples of $C_{1-4}$alkyl and $C_{1-6}$alkyl include methyl, ethyl, propyl, isopropyl, sec-butyl and tert-butyl; examples of $C_{1-4}$alkoxy include methoxy, ethoxy, propoxy and tert-butoxy; examples of N—($C_{1-4}$alkyl)amino include methylamino, ethylamino and isopropylamino; examples of N,N—($C_{1-4}$alkyl)$_2$amino include dimethylamino, N-methyl-N-ethylamino and N-ethyl-N-isopropylamino; examples of carbocyclylidenyl are cyclopentylidenyl and 2,4-cyclohexadien-1-ylidenyl.

It is to be understood that, insofar as certain of the compounds of formula (I) defined below may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK.

Suitable compounds of formula (I) are those wherein any one or more of the following apply. Such values may be used where appropriate with any of the definitions, claims or embodiments defined hereinbefore or hereinafter.

Ring A is pyridin-2-yl optionally substituted on carbon by one or more groups selected from $R^4$.

Ring A is thiazol-2-yl optionally substituted on carbon by one or more groups selected from $R^4$.

Ring A is pyridin-2-yl or thiazol-2-yl; wherein said pyridin-2-yl or thiazol-2-yl may be optionally substituted on carbon by one or more groups selected from $R^4$ wherein: $R^4$ is carboxy.

Ring A is unsubstituted or is substituted by carboxy.

Ring A is pyridin-2-yl, 5-carboxypyridin-2-yl, thiazol-2-yl or 5-carboxythiazol-2-yl.

Ring A is 5-carboxypyridin-2-yl, thiazol-2-yl or 5-carboxythiazol-2-yl.

$R^1$ is hydrogen and $R^2$ is $C_{1-4}$alkyl; wherein $R^2$ may be substituted on carbon by one or more groups selected from $R^5$.

$R^1$ is $C_{1-4}$alkyl and $R^2$ is hydrogen; wherein $R^1$ may be substituted on carbon by one or more groups selected from $R^5$.

One of $R^1$ and $R^2$ is hydrogen and the other is hydrogen or $C_{1-4}$alkyl.

$R^1$ is hydrogen or $C_{1-4}$alkyl and $R^2$ is hydrogen.

Both $R^1$ and $R^2$ are hydrogen.

$R^1$ is methyl or hydrogen and $R^2$ is hydrogen.

$R^3$ is selected from $C_{1-4}$alkoxy and carbocyclyloxy; wherein $R^3$ may be independently optionally substituted on carbon by one or more groups selected from $R^6$;

wherein: $R^6$ is selected from halo, carbocyclyl, heterocyclyl, carbocyclylidenyl; wherein $R^6$ may be optionally substituted on carbon by one or more $R^7$; wherein:
$R^7$ is selected from halo and methyl.

$R^3$ is selected from $C_{1-4}$alkoxy; wherein $R^3$ may be independently optionally substituted on carbon by one or more groups selected from $R^6$;

wherein: $R^6$ is selected from carbocyclyl and heterocyclyl; wherein $R^6$ may be optionally substituted on carbon by one or more $R^7$; wherein:
$R^7$ is selected from halo and methyl.

$R^3$ is selected from methoxy, ethoxy, iso-butoxy, phenoxy and benzocyclopent-1-yloxy; wherein $R^3$ may be independently optionally substituted on carbon by one or more groups selected from $R^6$;

wherein: $R^6$ is selected from fluoro, phenyl, isoxazolyl, thienyl and cyclopentlyidenyl; wherein $R^6$ may be optionally substituted on carbon by one or more $R^7$; wherein:
$R^7$ is selected from fluoro and methyl.

$R^3$ is selected from methoxy, ethoxy and iso-butoxy; wherein $R^3$ may be independently optionally substituted on carbon by one or more groups selected from $R^6$;

wherein: $R^6$ is selected from phenyl, isoxazolyl and thienyl; wherein $R^6$ may be optionally substituted on carbon by one or more $R^7$; wherein:
$R^7$ is selected from fluoro and methyl.

$R^3$ is selected from 2-fluorobenzyloxy, 5-methylisoxazol-3-ylmethoxy, 2-thien-3-ylethoxy, cyclopenylidenylmethoxy, 1-cyclopenylidenylethoxy, phenoxy, benzocyclopent-1-yloxy and 2-phenyl-2,2-difluoroethoxy.

$R^3$ is selected from 2-fluorobenzyloxy, 5-methylisoxazol-3-ylmethoxy and 2-thien-3-ylethoxy.

Therefore in a further aspect of the invention, there is provided a compound of formula (I) (as depicted above) wherein Ring A is pyridin-2-yl or thiazol-2-yl; wherein said pyridin-2-yl or thiazol-2-yl may be optionally substituted on carbon by one or more groups selected from $R^4$ wherein:

$R^4$ is carboxy;
$R^1$ is methyl or hydrogen and $R^2$ is hydrogen; and
$R^3$ is selected from $C_{1-4}$-alkoxy; wherein $R^3$ may be independently optionally substituted on carbon by one or more groups selected from $R^6$; wherein:
$R^6$ is selected from carbocyclyl and heterocyclyl; preferably phenyl, thienyl or isoxazolyl, wherein $R^6$ may be optionally substituted on carbon by one or more $R^7$; wherein:
$R^7$ is selected from halo and methyl;

or a salt, solvate or pro-drug thereof.

Therefore in a further aspect of the invention, there is provided a compound of formula (I) (as depicted above) wherein Ring A is 5-carboxypyridin-2-yl, thiazol-2-yl or 5-carboxythiazol-2-yl;
$R^1$ is methyl or hydrogen and $R^2$ is hydrogen; and
$R^3$ is selected from 2-fluorobenzyloxy, 5-methylisoxazol-3-ylmethoxy and 2-thien-3-ylethoxy;

or a salt, solvate or pro-drug thereof.

In another aspect of the invention, preferred compounds of the invention include:
2-methyl-4-isobutoxy-6-[N-(5-carboxypyridin-2-yl)carbamoyl]benzofuran;
2-methyl-4-(2-fluorophenylmethoxy)-6-[N-(5-carboxypyridin-2-yl)carbamoyl]benzofuran;
2-methyl-4-isobutoxy-6-[N-(5-carboxythiazol-2-yl)carbamoyl]benzofuran;
2-methyl-4-(5-methylisoxazol-3-ylmethoxy)-6-[N-(5-carboxypyridin-2-yl)carbamoyl]benzofuran;
4-(2-fluorophenylmethoxy)-6-[N-(5-carboxypyridin-2-yl)carbamoyl]benzofuran;
4-(5-methylisoxazol-3-ylmethoxy)-6-[N-(5-carboxypyridin-2-yl)carbamoyl]benzofuran;
2-methyl-4-(thien-2-ylethoxy)-6-[N-(5-carboxypyridin-2-yl)carbamoyl]benzofuran; and
2-methyl-4-isobutoxy-6-[N-(thiazol-2-yl)carbamoyl]benzofuran or a salt, solvate or pro-drug thereof.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen;
c) H. Bundgaard, Chapter 5 "Design and Application of Prodrugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988); and
f) N. Kakeya, et al., Chem Pharm Bull, 32, 692 (1984).

The contents of the above cited documents are incorporated herein by reference.

Examples of pro-drugs are as follows. An in vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$-$C_6$alkoxymethyl esters for example methoxymethyl, $C_1$-$C_6$alkanoyloxymethyl esters for example pivaloyloxymethyl, phthalidyl esters, $C_3$-$C_8$cycloalkoxycarbonyloxy$C_1$-$C_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in vivo hydrolysable ester of a compound of the invention containing a hydroxy group includes inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethyl-propionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

A further feature of the invention is a pharmaceutical composition comprising a compound of formula (I) as defined above, or a salt, solvate or prodrug thereof, together with a pharmaceutically-acceptable diluent or carrier.

According to another aspect of the invention there is provided a compound of formula (I) as defined above for use as a medicament.

Further according to the invention there is provided a compound of formula (I) for use in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially type 2 diabetes, by administering an effective amount of a compound of formula (I), or salt, solvate or pro-drug thereof, to a mammal in need of such treatment.

Specific disease which may be treated by the compound or composition of the invention include: blood glucose lowering in diabetes mellitus type 2 without a serious risk of hypoglycaemia (and potential to treat type 1), dyslipidemea, obesity, insulin resistance, metabolic syndrome X, impaired glucose tolerance.

As discussed above, thus the GLK/GLKRP system can be described as a potential "diabesity" target (of benefit in both diabetes and obesity). Thus, according to another aspect of the invention there if provided the use of a compound of formula (I), or salt, solvate or pro-drug thereof, in the preparation of a medicament for use in the combined treatment or prevention of diabetes and obesity.

According to another aspect of the invention there if provided the use of a compound of formula (I), or salt, solvate or pro-drug thereof, in the preparation of a medicament for use in the treatment or prevention of obesity.

According to a further aspect of the invention there is provided a method for the combined treatment of obesity and diabetes by administering an effective amount of a compound of formula (I), or salt, solvate or pro-drug thereof, to a mammal in need of such treatment.

According to a further aspect of the invention there is provided a method for the treatment of obesity by administering an effective amount of a compound of formula (I), or salt, solvate or pro-drug thereof, to a mammal in need of such treatment.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the formula (I) will naturally vary according to the nature and severity of the conditions, the age and sex of the animal or patient and the route of administration, according to well known principles of medicine.

In using a compound of the formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example in the treatment of diabetes mellitus chemotherapy may include the following main categories of treatment:

1) Insulin and insulin analogues;

2) Insulin secretagogues including sulphonylureas (for example glibenclamide, glipizide) and prandial glucose regulators (for example repaglinide, nateglinide);

3) Insulin sensitising agents including PPARg agonists (for example pioglitazone and rosiglitazone);

4) Agents that suppress hepatic glucose output (for example metformin).

5) Agents designed to reduce the absorption of glucose from the intestine (for example acarbose);

6) Agents designed to treat the complications of prolonged hyperglycaemia;

7) Anti-obesity agents (for example sibutramine and orlistat);

8) Anti-dyslipidaemia agents such as, HMG-CoA reductase inhibitors (statins, e.g. pravastatin); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);

9) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);

10) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and 11) Anti-inflammatory agents, such as non-steroidal antiinfammatory drugs (eg. aspirin) and steroidal anti-inflammatory agents (eg. cortisone).

According to another aspect of the present invention there is provided individual compounds produced as end products in the Examples set out below and salts, solvates and pro-drugs thereof.

Another aspect of the present invention provides a process for preparing a compound of formula (I) or a salt, solvate or pro-drug thereof which process (wherein variable groups are, unless otherwise specified, as defined in formula (I)) comprises:

Process 1): reacting an acid of formula (II):

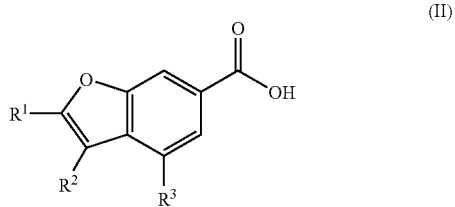

(II)

or an activated derivative thereof; with a compound of formula (II): or

(III)

Process 2) for compounds of formula (i) wherein $R^4$ is carboxy; deprotecting a compound of formula (III):

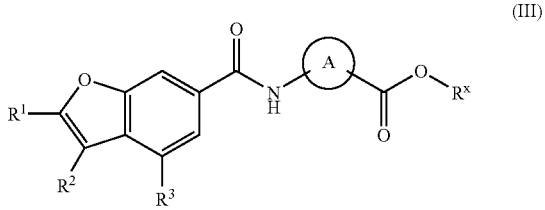

(III)

wherein $R^xC(O)O$— is an ester group;

and thereafter if necessary or desirable:

i) converting a compound of the formula (I) into another compound of the formula (I), and or;

ii) removing any protecting groups; and/or iii) forming a salt, solvate or pro-drug thereof.

Suitable activated acid derivatives include acid halides, for example acid chlorides, and active esters, for example pentafluorophenyl esters. The reaction of these types of compounds with amines is well known in the art.

The group $R^xOC(O)$— is an ester. Suitable values for $R^x$ are $C_{1-6}$alkyl and benzyl, particularly methyl and ethyl.

The reactions described above may be performed under standard conditions. The intermediates described above are commercially available, are known in the art or may be prepared by known procedures.

Some of the intermediates described herein are novel and are thus provided as a further feature of the invention. For example compounds of formula (III) are provided as a further feature of the invention.

During the preparation process, it may be advantageous to use a protecting group. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain $C_{1-12}$alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and $C_{2-6}$alkenyl groups (e.g. allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, acid-, base, metal- or enzymically-catalysed hydrolysis, or photolytically for groups such as o-nitrobenzyloxycarbonyl, or with fluoride ions for silyl groups.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/ arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

Biological Tests:

The biological effects of the compounds of formula (I) may be tested in the following way:

(1) Enzymatic activity of GLK may be measured by incubating GLK, ATP and glucose. The rate of product formation may be determined by coupling the assay to a G-6-P dehydrogenase, NADP/NADPH system and measuring the increase in optical density at 340 nm (Matschinsky et al 1993).

(2) A GLK/GLKRP binding assay for measuring the binding interactions between GLK and GLKRP. The method may be used to identify compounds which modulate GLK by modulating the interaction between GLK and GLKRP. GLKRP and GLK are incubated with an inhibitory concentration of F-6-P, optionally in the presence of test compound, and the extent of interaction between GLK and GLKRP is measured. Compounds which either displace F-6-P or in some other way reduce the GLK/GLKRP interaction will be detected by a decrease in the amount of GLK/GLKRP complex formed. Compounds which promote F-6-P binding or in some other way enhance the GLK/GLKRP interaction will be detected by an increase in the amount of GLK/GLKRP complex formed. A specific example of such a binding assay is described below.

GLK/GLKRP Scintillation Proximity Assay

Compounds of the invention were found to have an activity of less than 10 μm when tested in the GLK/GLKRP scintillation proximity assay described below.

Recombinant human GLK and GLKRP were used to develop a "mix and measure" 96 well SPA (scintillation proximity assay) as described in WO01/20327 (the contents of which are incorporated herein by reference). GLK (Biotinylated) and GLKRP are incubated with streptavidin linked SPA beads (Amersham) in the presence of an inhibitory concentration of radiolabelled [3H]F-6-P (Amersham Custom Synthesis TRQ8689), giving a signal. Compounds which either displace the P-6-P or in some other way disrupt the GLK/GLKRP binding interaction will cause this signal to be lost.

Binding assays were performed at room temperature for 2 hours. The reaction mixtures contained 50 mM Tris-HCl (pH 7.5), 2 mM ATP, 5 mM $MgCl_2$, 0.5 mM DTT, recombinant biotinylated GLK (0.1 mg), recombinant GLKRP (0.1 mg), 0.05 mCi [3H] F-6-P (Amersham) to give a final volume of 100 ml. Following incubation, the extent of GLK/GLKRP complex formation was determined by addition of 0.1 mg/well avidin linked SPA beads (Amersham) and scintillation counting on a Packard TopCount NXT.

(3) A F-6-P/GLKRP binding assay for measuring the binding interaction between GLKRP and F-6-P. This method may be used to provide further information on the mechanism of action of the compounds. Compounds identified in the GLK/ GLKRP binding assay may modulate the interaction of GLK and GLKRP either by displacing F-6-P or by modifying the GLK/GLKRP interaction in some other way. For example, protein-protein interactions are generally known to occur by interactions through multiple binding sites. It is thus possible that a compound which modifies the interaction between GLK and GLKRP could act by binding to one or more of several different binding sites.

The F-6-P/GLKRP binding assay identifies only those compounds which modulate the interaction of GLK and GLKRP by displacing F-6-P from its binding site on GLKRP.

GLKRP is incubated with test compound and an inhibitory concentration of F-6-P, in the absence of GLK, and the extent of interaction between F-6-P and GLKRP is measured. Compounds which displace the binding of F-6-P to GLKRP may be detected by a change in the amount of GLKRP/F-6-P complex formed. A specific example of such a binding assay is described below.

F-6-P/GLKRP Scintillation Proximity Assay

Recombinant human GLKRP was used to develop a "mix and measure" 96 well scintillation proximity assay ) as described in WO01/20327 (the contents of which are incorporated herein by reference). FLAG-tagged GLKRP is incubated with protein A coated SPA beads (Amersham) and an anti-FLAG antibody in the presence of an inhibitory concentration of radiolabelled [3H]F-6-P. A signal is generated. Compounds which displace the F-6-P will cause this signal to be lost. A combination of this assay and the GLK/GLKRP binding assay will allow the observer to identify compounds which disrupt the GLK/GLKRP binding interaction by displacing F-6-P.

Binding assays were performed at room temperature for 2 hours. The reaction mixtures contained 50 mM Tris-HCl (pH 7.5), 2 mM ATP, 5 mM $MgCl_2$, 0.5 mM DTT, recombinant FLAG tagged GLKRP (0.1 mg), Anti-Flag M2 Antibody (0.2 mg) (IBI Kodak), 0.5 mCi [3H]F-6-P (Amersham) to give a final volume of 100 ml. Following incubation, the extent of F-6-P/GLKRP complex formation was determined by addition of 0.1 mg/well protein A linked SPA beads (Amersham) and scintillation counting on a Packard TopCount NXT.

Production of Recombinant GLK and GLKRP:

Preparation of mRNA

Human liver total mRNA was prepared by polytron homogenisation in 4M guanidine isothiocyanate, 2.5 mM citrate, 0.5% Sarkosyl, 100 mM b-mercaptoethanol, followed by centrifugation through 5.7M CsCl, 25 mM sodium acetate at 135,000 g (max) as described in Sambrook J, Fritsch E F & Maniatis T, 1989.

Poly A+ mRNA was prepared directly using a FastTrack™ mRNA isolation kit (Invitrogen).

PCR Amplification of GLK and GLKRP cDNA Sequences

Human GLK and GLKRP cDNA was obtained by PCR from human hepatic mRNA using established techniques described in Sambrook, Fritsch & Maniatis, 1989. PCR primers were designed according to the GLK and GLKRP cDNA sequences shown in Tanizawa et al 1991 and Bonthron, D. T. et al 1994 (later corrected in Warner, J. P. 1995).

Cloning in Bluescript II Vectors

GLK and GLKRP cDNA was cloned in *E. coli* using pBluescript II, (Short et al 1998) a recombinant cloning vector system similar to that employed by Yanisch-Perron C et al (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

Transformations

*E. Coli* transformations were generally carried out by electroporation. 400 ml cultures of strains DH5a or BL21(DE3) were grown in L-broth to an OD 600 of 0.5 and harvested by centrifugation at 2,000 g. The cells were washed twice in ice-cold deionised water, resuspended in 1 ml 10% glycerol and stored in aliquots at −70° C. Ligation mixes were desalted using Millipore V Series™ membranes (0.0025 mm) pore size). 40 ml of cells were incubated with 1 ml of ligation mix or plasmid DNA on ice for 10 minutes in 0.2 cm electroporation cuvettes, and then pulsed using a Gene Pulser™ apparatus (BioRad) at 0.5 kVcm$^{-1}$, 250 mF, 250. Transformants were selected on L-agar supplemented with tetracyline at 10 mg/ml or ampicillin at 100 mg/ml.

Expression

GLK was expressed from the vector pTB375NBSE in *E.coli* BL21 cells, producing a recombinant protein containing a 6-His tag immediately adjacent to the N-terminal methionine. Alternatively, another suitable vector is pET21 (+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in *E. coli* BL21 cells, producing a recombinant protein containing a C-terminal FLAG tag. The protein was purified initially by DEAE Sepharose ion exchange followed by utilisation of the FLAG tag for final purification on an M2 anti-FLAG immunoaffinity column purchased from Sigma-Aldrich (cat no. A1205).

Biotinylation of GLK:

GLK was biotinylated by reaction with biotinamidocaproate N-hydroxysuccinimide ester (biotin-NHS) purchased from Sigma-Aldrich (cat no. B2643). Briefly, free amino groups of the target protein (GLK) are reacted with biotin-NHS at a defined molar ratio forming stable amide bonds resulting in a product containing covalently bound biotin. Excess, non-conjugated biotin-NHS is removed from the product by dialysis. Specifically, 7.5 mg of GLK was added to 0.31 mg of biotin-NHS in 4 mL of 25 mM HEPES pH7.3, 0.15M KCl, 1 mM dithiothreitol, 1 mM EDTA, 1 mM MgCl$_2$ (buffer A). This reaction mixture was dialysed against 100 mL of buffer A containing a further 22 mg of biotin-NHS. After 4 hours excess biotin-NHS was removed by extensive dialysis against buffer A.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the formula (I) were confirmed by nuclear (generally proton) magnetic resonance (NMR) and mass spectral techniques; proton magnetic resonance chemical shift values were measured on the delta scale in deuterated dimethyl sulphoxide unless otherwise stated, and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Silica gel 60, 0.040-0.063 mm, 230-400 mesh); and (vi) where a "Bondelut" column is referred to, this means a column containing 10 g or 20 g or 50 g or 70 g of silica of 40 micron particle size, the silica being contained in a 60 ml disposable syringe and supported by a porous disc, obtained from Varian, Harbor City, Calif., USA under the name "Mega Bond Elut SI"; "Mega Bond Elut" is a trademark;

(vii) the following abbreviations are used:

DCM dichloromethane;

DMF dimethylformamide;

LCMS liquid chromatography/mass spectroscopy;

THF tetrahydrofuran.

EXAMPLE 1

2-Methyl-4-isobutoxy-6-[N-(5-carboxypyridin-2-yl) carbamoyl]benzofuran

Sodium hydroxide solution (0.94 ml of 1M, 0.94 mM) was added to a solution of 2-methyl-4-isobutoxy-6-[N-(5-methoxycarbonylpyridin-2-yl)carbamoyl]benzofuran (Method 1; 120 mg, 0.314 mM) in a methanol/THF mixture (1 ml+4 ml), and the resulting solution stirred at ambient temperature. After 4 hrs the reaction mixture was diluted with water (5 ml) and concentrated to half volume in vacuo. The resulting mixture was acidified to pH6 with 1M HCl. The resulting solid precipitate was filtered, washed with water, and dried to give a pale cream solid. This was chromatographed (10 g Bondelut), eluting with DCM containing methanol (0-10% gradient) to give the title compound as a colourless solid. NMR: 1.03 (d, 6H), 2.09 (sept, 1H), 2.45 (s, 3H), 3.97 (d, 2H), 6.66 (s, 1H), 7.44 (s, 1H), 7.85 (s, 1H), 8.31 (t, 2H), 8.87 (s, 1H), 11.10 (bs, 1H); m/z 367 (M+H)$^+$.

EXAMPLES 2-7

The following compounds were prepared by the procedure of Example 1 starting from the appropriate ester.

| Ex | Structure | NMR | MS | SM |
|---|---|---|---|---|
| 2 | 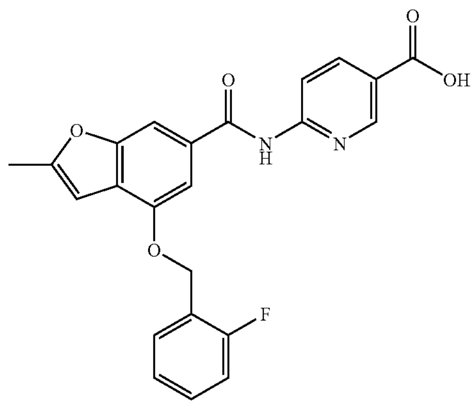 | 2.46 (s, 3H), 5.39 (s, 2H), 6.71 (s, 1H), 7.26 (m, 2H), 7.43 (m, 1H), 7.65 (m, 2H), 7.91 (s, 1H), 8.31 (m, 2H), 8.88 (s, 1H), 11.14 (bs, 1H), COOH not seen | (M + H)+ 421 | Method 17 |
| 3 | 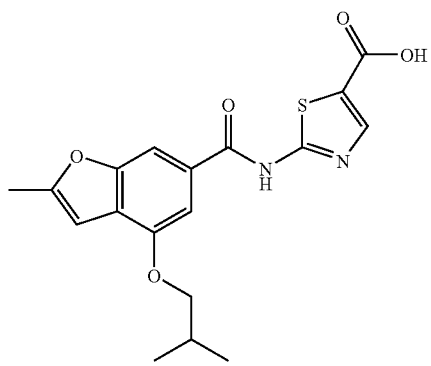 | 1.03 (d, 6H), 2.10 (sept, 1H), 2.46 (s, 3H), 3.96 (d, 2H), 6.66 (s, 1H), 7.51 (s, 1H), 7.92 (s, 1H), 8.14 (s, 1H), 12.20 (bs, 1H), COOH not seen | (2M + H)+ 749 | Method 18 |
| 4 | 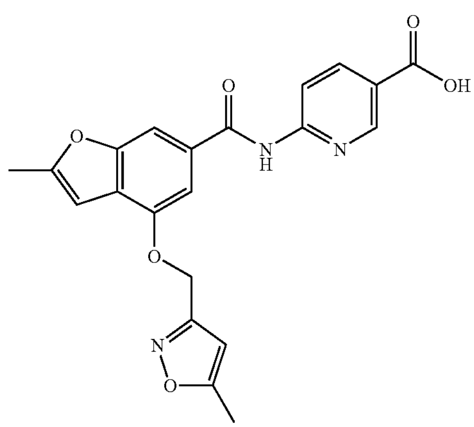 | 2.44 (s, 3H), 2.49 (s, 3H), 5.43 (s, 2H), 6.42 (s, 1H), 6.71 (s, 1H), 7.66 (s, 1H), 7.93 (s, 1H), 8.36 (m, 2H), 8.90 (s, 1H), 13.10 (bs, 1H), COOH not seen | (M + H)+ 408 | Method 19 |
| 5 | 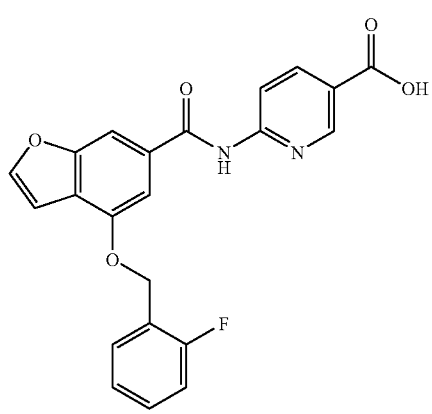 | 5.41 (s, 2H), 7.03 (s, 1H), 7.30 (m, 2H), 7.44 (m, 1H), 7.64 (m, 2H), 8.00 (s, 1H), 8.08 (d, 1H), 8.33 (m, 2H), 8.89 (s, 1H), 11.21 (bs, 1H), COOH not seen | (M + H)+ 407 (M − H)− 405 | Method 20 |

-continued

| Ex | Structure | NMR | MS | SM |
|---|---|---|---|---|
| 6 | 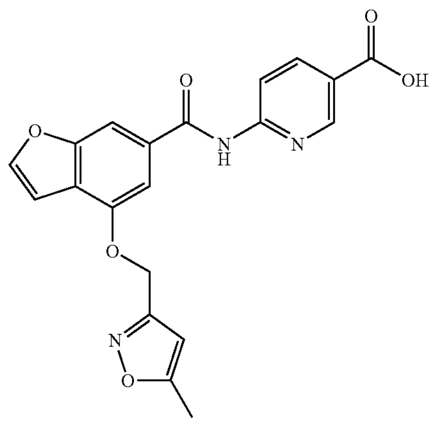 | 2.42 (s, 3H), 5.43 (s, 2H), 6.41 (s, 1H), 7.04 (d, 1H), 7.65 (s, 1H), 8.00 (s, 1H), 8.10 (d, 1H), 8.33 (m, 2H), 8.88 (s, 1H), 11.37 (bs, 1H), COOH not seen | (M + H)+ 394 (M − H)− 392 | Method 21 |
| 7 | 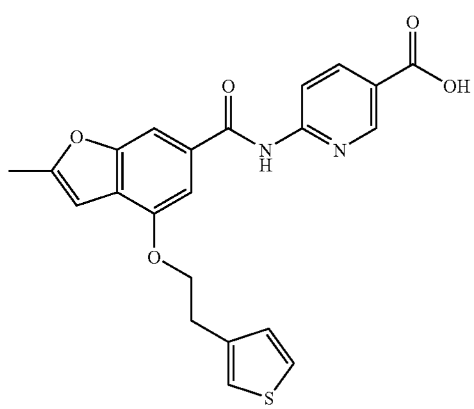 | 2.44 (s, 3H), 3.13 (t, 2H), 4.41 (t, 2H), 6.64 (s, 1H), 7.14 (d, 1H), 7.35 (m, 1H), 7.47 (m, 2H), 7.84 (s, 1H), 8.32 (m, 2H), 8.86 (s, 1H), 11.12 (bs, 1H), COOH not seen | (M + H)+ 423 | Method 22 |

EXAMPLE 8

The following compound was prepared by the procedure of Method 1 using 2-aminothiazole.

| Ex | Structure | NMR | MS |
|---|---|---|---|
| 8 | 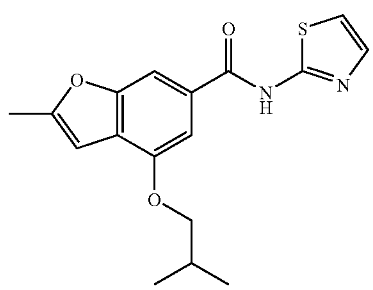 | 1.07 (d, 6H), 2.30 (sept, 1H), 2.50 (s, 3H), 4.01 (d, 2H), 6.60 (s, 1H), 7.27 (d, 1H), 7.52 (s, 1H), 7.58 (d, 1H), 7.92 (s, 1H), 12.56 (bs, 1H) | (M + H)+ 331 (2M + H)+ 661 |

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1

2-Methyl-4-isobutoxy-6-[N-(5-methoxycarbonylpyridin-2-yl)carbamoyl]benzofuran Oxalyl chloride (410 mg, 282 µl, 3.225 mmol, 5 eq) was added to a solution of 2-methyl-4-isobutoxy-6-carboxybenzofuran (Method 2; 0.160 mg, 0.645 mmol) in DCM (5 ml) and the reaction mixture stirred for 4 hrs at ambient temperature. Further reagent was added, the reaction mixture stirred for 16 hrs, and then warmed to 40° C. As starting acid still remained, the solvent was removed in vacuo and the residue treated with neat oxalyl chloride. The reaction mixture was then concentrated in vacuo and dissolved in pyridine (5 ml); to the resulting solution was added methyl 2-aminopyridine-5-carboxylate (98 mg, 0.645 mmol). After stirring for 16 hrs the reddish solution was concentrated in vacuo and the resulting gum dissolved in DCM and chromatographed (20 g Bondelut, eluting with hexane containing ethyl acetate, 0-100%) to give the title compound (122 mg, 49.5% yield) as a colourless gum which slowly set solid; LC-MS 383 (M+H)$^+$, 94.4% strength.

Method 2

2-Methyl-4-isobutoxy-6-carboxybenzofuran

Sodium hydroxide solution (2.28 ml of 1M, 2.28 mmol, 3 eq) was added to a solution of 2-methyl-4-isobutoxy-6-methoxycarbonylbenzofuran (Method 7; 200 mg, 0.76 mmol; contained ca 15 mol % of isobutyl ester) in MeOH (2.28 ml)/THF (2.28 ml). After 2 hours at 50° C. the reaction mixture was stirred at ambient temperature overnight and then concentrated to half-volume in vacuo. The resulting solution was diluted with water and acidified to pH 5 (1M HCl), and the resulting flocculent precipitate filtered and dried to give the title compound as a colourless solid (165 mg, 88%). NMR: 1.02 (d, 6H), 2.06 (sept, 1H), 2.45 (s, 3H), 3.90 (d, 2H), 6.64 (s, 1H), 7.24 (s, 1H), 7.64 (s, 1H), 12.83 (bs, 1H); m/z 247 (M−H)$^-$, 94.6% by LC-MS.

Methods 3-6

The following compounds were prepared by the procedure of Method 2.

| Method | Compound | SM |
|---|---|---|
| 3 | 2-Methyl-4-(2-fluorobenzyloxy)-6-carboxybenzofuran | Method 8 |
| 4 | 2-Methyl-4-(5-methylisoxazol-3-ylmethoxy)-6-carboxybenzofuran | Method 9 |
| 5 | 4-(2-Fluorobenzyloxy)-6-carboxybenzofuran | Method 10 |
| 6 | 4-(5-Methylisoxazol-3-ylmethoxy)-6-carboxybenzofuran | Method 11 |

Method 7

2-Methyl-4-isobutoxy-6-methoxycarbonylbenzofuran

2-Methyl-4-hydroxy-6-methoxycarbonylbenzofuran (Method 12; 412 mg, assumed 1.0 mmol) was stirred in anhydrous DMF (10 ml) and the solution treated sequentially with potassium carbonate (690 mg, 5 mmol, 5 eq) and 1-iodo-2-methylpropane (442 mg, 276 µl, 2.4 mmol, 2.4 eq). The reaction mixture was stirred at 90° C. for 3 hours, then cooled and poured into water; the resulting mixture was extracted twice with ethyl acetate, the extracts dried (MgSO$_4$) and evaporated in vacuo to yield a brown oil. This was chromatographed (50 g Bondelut, eluting with hexane containing ethyl acetate, 0-100%) to give the title compound as a clear oil contaminated with ca 15% of the corresponding iso-butyl ester. NMR: 1.02 (d, 6H), 2.06 (sept, 1H), 2.45 (s, 3H), 3.84 (s, 3H), 3.91 (d, 2H), 6.66 (s, 1H), 7.24 (s, 1H), 7.66 (s, 1H); the spectrum also contained signals consistent with isobutyl ester, ca 15 mol %.

Methods 8-11

The following compounds were prepared by the procedure of Method 7.

| Method | Compound | SM |
|---|---|---|
| 8 | 2-Methyl-4-(2-fluorobenzyloxy)-6-methoxycarbonylbenzofuran | Method 12 |
| 9 | 2-Methyl-4-(5-methylisoxazol-3-ylmethoxy)-6-methoxycarbonylbenzofuran | Method 12 |
| 10 | 4-(2-Fluorobenzyloxy)-6-methoxycarbonylbenzofuran | Method 13 |
| 11 | 4-(5-Methylisoxazol-3-ylmethoxy)-6-methoxycarbonylbenzofuran | Method 13 |

Method 12

2-Methyl-4-hydroxy-6-methoxycarbonylbenzofuran

2-Methyl-4-acetoxy-6-methoxycarbonylbenzofuran (Method 14; 1.275 g, 5.14 mmol) was added to a suspension of potassium carbonate (1.408 g, 10.3 mmol, 2 eq) in MeOH (100 ml) and water (2 ml), and the mixture stirred for 1 hr at ambient temperature. The supernatant liquor was decanted from the insoluble material and evaporated in vacuo to yield a cream solid (2.19 g, assumed to be contaminated with inorganics). NMR: 2.35 (s, 3H), 3.56 (br s, 1H), 3.73 (s, 3H), 6.46 (s, 1H), 6.69 (s, 1H), 6.86 (s, 1H); m/z 205 (M−H)$^-$, 83% by LC-MS.

Method 13

The following compound was prepared by the procedure of Method 12 starting from 4-acetoxy-6-methoxycarbonylbenzofuran (J Chem Soc (C); 1968, 867-9).

| Method | Compound |
|---|---|
| 13 | 4-Hydroxy-6-methoxycarbonylbenzofuran |

Method 14

2-Methyl-4-acetoxy-6-methoxycarbonylbenzofuran

A mixture of E-3-methoxycarbonyl-4-(5-methylfur-2-yl)-but-3-enoic acid (Method 15; 1.39 g, 6.2 mmol) and potassium acetate (620 mg, 6.3 mmol) in acetic anhydride (12.5 ml) was heated at 140° C. for 15 mins. The reaction mixture was cooled and poured on to a water/ethyl acetate mixture; the aqueous layer was separated and the organic layer washed sequentially with saturated sodium bicarbonate solution and brine, dried (MgSO$_4$) and evaporated in vacuo to yield the crude product as a dark crystalline mass. This was chromatographed (50 g Bondelut, eluting with hexane containing ethyl acetate, 0-100%) to give the title compound as a pale yellow solid, 1.42 g (92%). NMR: 2.36 (s, 3H), 3.34 (s, 3H), 3.87 (s, 3H), 6.68 (s, 1H), 7.56 (s, 1H), 7.96 (s, 1H); m/z 247 (M−H)$^-$, 97.1% by LC-MS.

Method 15

E-3-Methoxycarbonyl-4-(5-methylfur-2-yl)-but-3-enoic acid

A solution of E-3-methoxycarbonyl-4-(5-methylfur-2-yl)-but-3-enoic acid t-butyl ester (Method 16; 1.39 g, 4.96 mmol) in trifluoroacetic acid/water (20 ml of 90:10 v/v) was stirred at ambient temperature for 20 mins; the reaction mixture was then diluted with toluene (30 ml) and evaporated in vacuo to yield a brown oil. After further azeotroping with toluene (30 ml), this set solid; trituration with isohexane and collection of the residue yielded the title compound as a brown solid (1.05 g, 95%). NMR 2.33 (s, 3H), 3.65 (s, 2H), 3.72 (s, 3H), 6.29 (d, 1H), 6.85 (d, 1H), 7.41 (s, 1H), 12.34 (bs, 1H).

Method 16

E-3-methoxycarbonyl-4(5-methylfur-2-yl)-but-3-enoic acid t-butyl ester

A solution of 1-methoxycarbonyl-2-t-butoxycarbonyl ethyl phosphorane (JCS Perkin II, 1975, p1030; 2.69 g, 6 mmol, 1.2 eq) and 5-methylfuran-2-al (0.5 ml, 5 mmol) in dry toluene (10 ml) was stirred at 80° C. for 48 hrs, and then evaporated to dryness. The residue was chromatographed (50 g Bondelut, eluting with hexane containing 10% v/v ethyl acetate) to yield the title compound as a brown oil (1.39 g, 100%). NMR: 1.38 (s, 9H), 2.33 (s, 3H), 3.62 (s, 2H), 3.71 (s, 3H), 6.31 (d, 1H), 6.85 (d, 1H), 7.42 (s, 1H).

Method 17

2-Methyl-4-(2-fluorobenzyloxy)-6-[N-(4-methoxycarbonylphenyl)carbamoyl]benzofuran A solution of 2-methyl-4-(2-fluorobenzyloxy)-1-benzofuran-6-carboxylic acid (Method 3; 0.60 mg, 0.2 mmol) and methyl 2-aminopyridine-5-carboxylate (61 mg, 0.4 mmol, 2 eq) in pyridine (1 ml) was treated with phosphorus oxychloride (20.5 µl, 0.22 mmol, 1.1 eq), and the reaction mixture stirred for 16 hrs at ambient temperature. The reaction mixture was poured into water and extracted twice with ethyl acetate; the extracts were washed with brine, dried (MgSO$_4$) and evaporated to give a yellow gum. This was chromatographed (10 g Bondelut, eluting with hexane containing ethyl acetate, 0-100%) to give the title compound as a solid (61 mg, 70%). NMR: 2.46 (s, 3H), 3.87 (s, 3H), 5.37 (s, 2H), 6.66 (s, 1H), 7.25 (m, 2H), 7.42 (m, 1H), 7.62 (m, 2H), 7.91 (s, 1H), 8.36 (m, 2H), 8.91 (s, 1H), 11.20 (bs, 1H); m/z 435 (M+H)$^+$, 100% by LC-MS.

Methods 18-22

The following compounds were prepared by the procedure of Method 17.

| Method | Compound | SM |
|---|---|---|
| 18 | 2-Methyl-4-isobutoxy-6-[N-(5-ethoxycarbonylthiazol-2-yl)carbamoyl]benzofuran | Method 2 |
| 19 | 2-Methyl-4-(5-methylisoxazol-3-ylmethoxy)-6-[N-(5-methoxycarbonylpyridin-2-yl)carbamoyl]benzofuran | Method 4 |
| 20 | 4-(2-Fluorobenzyloxy)-6-[N-(5-methoxycarbonylpyridin-2-yl)carbamoyl]benzofuran | Method 5 |
| 21 | 4-(5-Methylisoxazol-3-ylmethoxy)-6-[N-(5-methoxycarbonylpyridin-2-yl)carbamoyl]benzofuran | Method 6 |
| 22 | 2-Methyl-4-(2-thien-3-ylethoxy)-6-[N-(5-methoxycarbonylpyridin-2-yl)carbamoyl]benzofuran | Method 23 |

Method 23

2-Methyl-4-(2-thien-3-ylethoxy)-6-methoxycarbonylbenzofuran

To a solution of 2-methyl-4-hydroxy-6-methoxycarbonylbenzofuran (Method 12; 1.24 g, 6.0 mmol) and 2-(3-thienyl)ethanol (768 mg, 0.67 ml, 6.0 mmol) in DCM (DCM, 50 ml) was added polymer-supported triphenyl phosphine (2.5 g, ca 3 mmol/g, 1.5 eq), and the suspension cooled to 5° C. under an argon atmosphere. To this was added di t-butyl azodicarboxylate (1.725 g, 7.5 mmol, 1.5 eq), and the reaction mixture stirred overnight, allowing to warm to ambient temperature. It was then filtered through diatomaceous earth, washed through with DCM, and the filtrate and washings evaporated in vacuo to ~50 ml total volume. To this was added trifluoroacetic acid (2 ml), and the solution evaporated in vacuo to give a red oil. This was chromatographed (70 g Bondelut, eluting with hexane containing ethyl acetate, 0-50%) to give a red solid; this was re-chromatographed (as previous) to give the title compound as a colourless crystalline solid (150 mg, 8% yield). NMR: 2.46 (s, 3H), 3.10 (t, 2H), 3.83 (s, 3H), 4.33 (t, 2H), 6.64 (s, 1H), 7.12 (dd, 1H), 7.28 (s, 1H), 7.32 (d, 1H), 7.46 (dd, 1H), 7.66 (s, 1H).

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |

| -continued | |
|---|---|
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |

| -continued | |
|---|---|
| 1-Dodecylazacycloheptan-2-one | 50 μl |
| Propylene glycol | to 1 ml |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

REFERENCES

1 Printz, R. L., Magnuson, M. A. and Granner, D. K. (1993) Annual Review of Nutrition 13, 463-96

2 DeFronzo, R. A. (1988) Diabetes 37, 667-87

3 Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697-702

4 Bell, G. I., Pilkis, S. J., Weber, I. T. and Polonsky, K. S. (1996) Annual Review of Physiology 58, 171-86

5 Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755-61

6 Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240-6

7 Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226-30

8 Caro, J. F., Triester, S., Patel, V. K., Tapscott, E. B., Frazier, N. L. and Dohm, G. L. (1995) Hormone & Metabolic Research 27, 19-22

9 Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287-95

10 Shiota, M., Postic, C., Fujimoto, Y., Jetton, T. L., Dixon, K., Pan, D., Grimsby, J., Grippo, J. F., Magnuson, M. A. and Cherrington, A. D. (2001) Diabetes 50, 622-9

11 Ferre, T., Pujol, A., Riu, E., Bosch, F. and Valera, A. (1996) Proceedings of the National Academy of Sciences of the United States of America 93, 7225-30

12 Seoane, J., Barbera, A., Telemaque-Potts, S., Newgard, C. B. and Guinovart, J. J. (1999) Journal of Biological Chemistry 274, 31833-8

13 Moore, M. C., Davis, S. N., Mann, S. L. and Cherrington, A. D. (2001) Diabetes Care 24, 1882-7

14 Alvarez, E., Roncero, I., Chowen, J. A., Vazquez, P. and Blazquez, E. (2002) Journal of Neurochemistry 80, 45-53

15 Lynch, R. M., Tompkins, L. S., Brooks, H. L., Dunn-Meynell, A. A. and Levin, B. E. (2000) Diabetes 49, 693-700

16 Roncero, I., Alvarez, E., Vazquez, P. and Blazquez, E. (2000) Journal of Neurochemistry 74, 1848-57

17 Yang, X. J., Kow, L. M., Funabashi, T. and Mobbs, C. V. (1999) Diabetes 48, 1763-1772

18 Schuit, P. C., Huypens, P., Heimberg, H. and Pipeleers, D. G. (2001) Diabetes 50, 1-11

19 Levin, B. E. (2001) International Journal of Obesity 25

20 Alvarez, E., Roncero, I., Chowen, J. A., Thorens, B. and Blazquez, E. (1996) Journal of Neurochemistry 66, 920-7

21 Mobbs, C. V., Kow, L. M. and Yang, X. J. (2001) American Journal of Physiology—Endocrinology & Metabolism 281, E649-54
22 Levin, B. E., Dunn-Meynell, A. A. and Routh, V. H. (1999) American Journal of Physiology 276, R1223-31
23 Spanswick, D., Smith, M. A., Groppi, V. E., Logan, S. D. and Ashford, M. L. (1997) Nature 390, 521-5
24 Spanswick, D., Smith, M. A., Mirshamsi, S., Routh, V. H. and Ashford, M. L. (2000) Nature Neuroscience 3, 757-8
25 Levin, B. E. and Dunn-Meynell, A. A. (1997) Brain Research 776, 146-53
26 Levin, B. E., Govek, E. K. and Dunn-Meynell, A. A. (1998) Brain Research 808, 317-9
27 Levin, B. E., Brown, K. L. and Dunn-Meynell, A. A. (1996) Brain Research 739, 293-300
28 Rowe, I. C., Boden, P. R. and Ashford, M. L. (1996) Journal of Physiology 497, 365-77
29 Fujimoto, K., Sakata, T., Arase, K., Kurata, K., Okabe, Y. and Shiraishi, T. (1985) Life Sciences 37, 2475-82
30 Kurata, K., Fujimoto, K. and Sakata, T. (1989) Metabolism: Clinical & Experimental 38, 46-51
31 Kurata, K., Fujimoto, K., Sakata, T., Etou, H. and Fukagawa, K. (1986) Physiology & Behavior 37, 615-20

The invention claimed is:
1. A compound of formula (I) or a salt thereof,

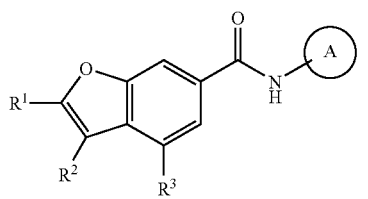

(I)

wherein:
Ring A is pyridin-2-yl wherein said pyridin-2-yl is optionally substituted on carbon by one or more groups selected from $R^4$;
one of $R^1$ and $R^2$ is hydrogen and the other is hydrogen or $C_{1-4}$alkyl; wherein $R^1$ and $R^2$ are optionally substituted on carbon by one or more groups selected from $R^5$;
$R^3$ is selected from $C_{1-4}$alkyl, $C_{1-4}$alkoxy, carbocyclyl, and carbocyclyloxy; wherein $R^3$ is optionally substituted on carbon by one or more groups selected from $R^6$;
$R^4$ is selected from halo, carboxy and $C_{1-4}$alkyl;
$R^5$ and $R^6$ are independently selected from halo, $C_{1-4}$alkyl, $C_{1-4}$alkoxy, N—($C_{1-4}$alkyl)amino, N,N—($C_{1-4}$alkyl)$_2$-amino, carbocyclyl, carbocyclyloxy, and carbocyclylidenyl; wherein $R^5$ and $R^6$ are independently optionally substituted on carbon by one or more $R^7$;
$R^7$ is selected from halo, carboxy, methyl, ethyl, methoxy, ethoxy, methylamino, ethylamino, dimethylamino, diethylamino and N-methyl-N-ethylamino.

2. The compound according to claim 1 or a salt thereof, wherein Ring A is unsubstituted or is substituted by carboxy.

3. The compound according to claim 2 or a salt thereof, wherein one of $R^1$ and $R^2$ is hydrogen and the other is hydrogen or $C_{1-4}$alkyl.

4. The compound according claim 1 or a salt thereof, wherein $R^3$ is selected from $C_{1-4}$alkoxy; wherein $R^3$ is optionally substituted on carbon by one or more groups selected from $R^6$.

5. The compound according to claim 1 or a salt thereof, wherein $R^3$ is 2-fluorobenzyloxy.

6. A compound according to claim 1 selected from:
2-methyl-4-isobutoxy-6-[N-(5-carboxypyridin-2-yl)carbamoyl]benzofuran;
2-methyl-4-(2-fluorophenylmethoxy)-6-[N-(5-carboxypyridin-2-yl)carbamoyl]benzofuran; and
4-(2-fluorophenylmethoxy)-6-[N-(5-carboxypyridin-2-yl)carbamoyl]benzofuran;
or a salt thereof.

7. A pharmaceutical composition comprising a compound according to any one of claim 1 to 6, or a salt thereof, together with a pharmaceutically acceptable diluent or carrier.

8. A method of treating type 2 diabetes, comprising administering an effective amount of a compound according to any one of claim 1 to 6 or a salt thereof.

* * * * *